United States Patent [19]

Hirayama et al.

[11] Patent Number: 5,031,418
[45] Date of Patent: Jul. 16, 1991

[54] COOLING PACK

[75] Inventors: Miyuki Hirayama; Eiji Umemura, both of Tokyo; Masatoshi Fujiwara, Kawasaki; Hiroyuki Inagaki, Yokohama, all of Japan

[73] Assignee: Uni-Charm Corporation, Ehime, Japan

[21] Appl. No.: 374,787

[22] Filed: Jul. 3, 1989

[30] Foreign Application Priority Data

Jul. 2, 1988 [JP] Japan ............................. 63-88115[U]
Jun. 12, 1989 [JP] Japan ............................. 1-68249[U]

[51] Int. Cl.⁵ .............................................. F25D 3/08
[52] U.S. Cl. ........................................ 62/530; 62/457.2
[58] Field of Search ................. 62/60, 529, 530, 372, 62/4, 457.2, 438

[56] References Cited

U.S. PATENT DOCUMENTS

| 2,568,975 | 9/1951 | Warne ............................. 62/530 X |
| 4,404,820 | 9/1983 | Romaine ...................... 62/457.2 X |
| 4,530,220 | 7/1985 | Nambu et al. ...................... 62/530 |
| 4,910,978 | 3/1990 | Gordon et al. ...................... 62/530 |

Primary Examiner—Lloyd L. King
Attorney, Agent, or Firm—Fred Philpitt

[57] ABSTRACT

A cooling pack comprises at least one coolant carrier (10) for keeping coolant held thereon and a container (11) adapted to enclose the coolant carrier (10). The coolant carrier (10) consists of liquid absorbent substrate (12) and liquid absorbent polymer particles (13). The container (11) has at least a pair of flat layers opposed to each other which are adapted to introduce liquid into the container (11). The cooling pack can provide beneficial features such as to avoid exudation of liquid absorbent polymer particles (13), to introduce liquid into the container (11) in a short period of time, and to obtain non-sticking of the container (11) refrigerated condition.

4 Claims, 5 Drawing Sheets

COOLING PACK

BACKGROUND OF THE INVENTION

The present invention relates to a cooling pack and, more particularly, to such a cooling pack comprising a coolant carrier obtained by dispersing and fixing liquid absorbent polymer particles on liquid absorbent substrate to keep said particles dispersed thereon, and a container adapted to enclose said coolant carrier.

It is well known, for example, from Japanese Disclosure Gazette Nos. 1987-267386 and 1987-240377 to utilize as a coolant carrier water absorbent polymers to obtain a cooling effect for a long duration and to avoid exudation of said polymer by fixing particles of said absorbent polymer to a suitable substrate. Such coolant carrier of prior art otherwise might be susceptible to said exudation or scattering and also to the occurrence of adhesive stickiness while in use and thawing of coolant. Accordingly, such a coolant carrier has usually been used in practice with an associated bag adapted to enclose said coolant carrier for improvement of shape stability as well as convenience of handling thereof.

With the articles of such nature, an adequate quantity of water is introduced into the bag so as to be held by absorbent polymer particles and then frozen prior to use. Means for introduction of water into said bag may be roughly classified into two types, i.e., a valve type means adapted for introduction of water into the sealed bag through a valve such as a check valve, and a dip type means adapted for introduction of water into the bag provided with a plurality of fine perforations or slits by immersing into water, through said fine perforations or slits. The valve type means for introduction of water has been found to be disadvantageous not only in that provision of the valve correspondingly increases the manufacturing cost thereof, but also in that it is impossible to introduce water into a plurality of said bags simultaneously, namely, water must be introduced into each of said bags one at a time. The dip type means allows water to be introduced into a plurality of said bags simultaneously, but is inconvenient in that a relatively long time is needed for introduction of water since a dimension of said fine perforations or slits is strictly limited to prevent leakage of the absorbent polymer particles possibly occurring before and after said water introduction, and also in that absorbent polymer particles tend to agglomerate to cause uneven water introduction into said bag.

SUMMARY OF THE INVENTION

It is one object of the present invention to provide a cooling pack being able to avoid the exudation of said liquid-absorbent polymer particles before and after introduction of said liquid, to introduce said liquid into said cooling pack in a short period of time, to provide substantially uniform liquid introduction into said cooling pack, and therefore to obtain beneficial cooling effects.

It is another object of the present invention to provide cooling packs of which the containers do no stick to one another even if a plurality of said containers are stacked on one another, the liquid-permeable layer sections of said containers contain a certain amount of water residue and such residual water is frozen.

The objects as have been set forth above are achieved, in accordance with the present invention, by a cooling pack comprising at least one coolant carrier consisting of a liquid absorbent substrate and liquid absorbent polymer particles dispersed and fixed thereon with substantially uniform distribution. Obviously, said coolant carrier is enclosed by said container.

According to a preferred embodiment, at least one of flat layers forming said container upon which another container can be successively stacked includes at least along a central section a liquid-impermeable layer section which covers at least a major portion of said coolant carrier opposed thereto.

According to another preferred embodiment, said liquid absorbent substrate is made of fibrous material and, for introduction of water into said container, at least one flat layer section of said container is formed by liquid-permeable fibrous nonwoven fabric. For said liquid-impermeable layer section, said section may be formed by a liquid-impermeable plastic sheet or film, or the liquid-permeable nonwoven fabric may be provided with such a liquid-impermeable plastic sheet or film, at least along a central inside thereof to provide said liquid-impermeable layer section.

According to still another preferred embodiment, said container is bag-shaped or box-shaped.

The cooling pack thus constructed in accordance with the present invention can be used, after an adequate amount of water has been introduced into said container so as to be absorbed and thereby held by said coolant carrier followed by freezing process therefor, for example, to maintain freshness of perishable foods, without taking out said coolant carrier from said container.

PREFERRED EMBODIMENTS

The present invention will now be described by way of examples with reference to the accompanying drawings.

Figure 1:
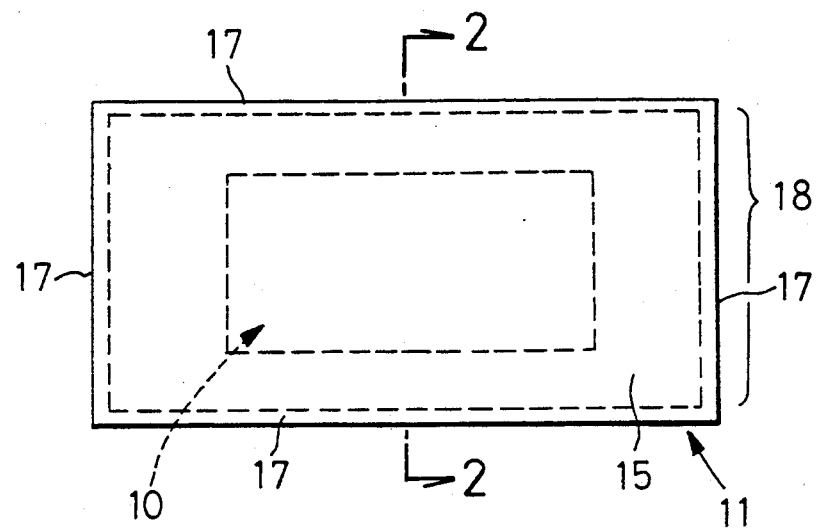
FIG. 1 is a plan view of an embodiment of the cooling pack constructed according to the present invention.
Figure 2:
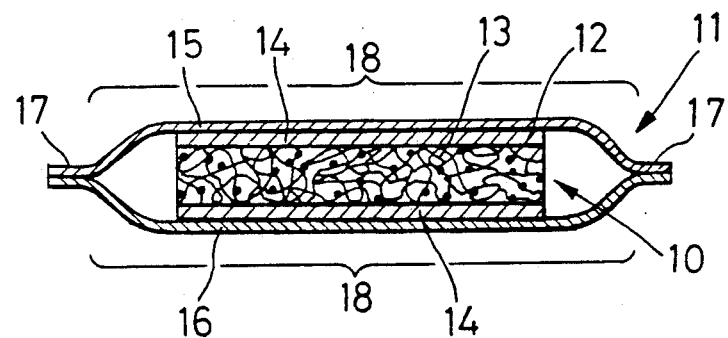
FIG. 2 is a sectional view taken along a line 2—2 in FIG. 1.

Referring to FIGS. 1 and 2, a cooling pack generally comprises a coolant carrier 10 in the form of a square sheet or mat and a container 11 enclosing said coolant carrier 10 which comprises, in turn, liquid absorbent polymer particles 13 dispersed and fixed on liquid absorbent (referred to hereinafter also as liquid-permeable) substrate 12. Such coolant carrier may be sheet comprising, for example, tissue layers having the liquid absorbent polymer particles sandwiched therebetween. However, in order to obtain uniform liquid absorption by said coolant carrier, it is preferred to adopt a coolant carrier comprising a liquid absorbent, particularly, a liquid absorbent and fibrous substrate containing the liquid absorbent polymer particles dispersed and fixed thereon with uniform distribution.

When it is said that the liquid absorbent polymer particles are dispersed and fixed on the fibrous substrate, a condition is referred to in which the liquid absorbent polymer preferably, in the form of substantially spheric particles, partially encloses component fibers of said fibrous substrate and, more specifically, the liquid absorbent polymer particles are physically integrated with these fibers. The term used herein "uniform distribution" is not limited to a condition in which a quantity of the liquid absorbent polymer particles dispersed and fixed on the liquid absorbent subtrate per unit volume or unit area of the latter is constant independently of locations, but covers also a condition in which the liquid absorbent polymer particles are dispersed and fixed on the liquid absorbent substrate with regular repetition of dots or stripes pattern. In general, this term implies a condition in which the liquid absorbent polymer particles are dispersed and fixed on the liquid absorbent substrate with a uniform distribution as a whole.

The liquid absorbent polymer particles being useful for the present invention should be able to absorb a quantity of water several ten times to several hundred times of their own weight and may be powdery polymers which have conventionally been popular such as various types of starch polyacrylate, polyvinylalcohol and polyester.

As the liquid absorbent fibrous substrate to which the liquid absorbent polymer particles are dispersed and fixed, card, airy web, tissue paper, nonwoven fabric, etc may be used. Preferably, hydrophilic fibers such as pulp fiber and rayon fiber, hydrophobic fibers such as polyester and polypropyrene, or mixture or combination thereof may be used in loosely molded or heat set condition to obtain a shape stability of said substrate.

Dispersion and fixation of super absorbent polymer particles onto the fibrous substrate is specifically achieved by processing the fibrous substrate with aqueous monomer solution containing, as its main ingredient, acrylate or mixed acrylate/methacrylate of alkali metal or ammonium and then polymerizing with aqueous raidcal polymerization initiator. The fibrous substrate may be wetted with said aqueous monomer solution by spraying or coating thereof.

Permeation and diffusion of the aqueous monomer solution into the fibrous substrate depend upon various factors such as the surface tension of the aqueous monomer solution, the specific gravity and the density of the fibrous substrate, and the angle at which the component fibers come in contact with the aqueous solution. These factors define together a state of dispersion and fixation of the aqueous monomer solution, and therefore of the polymer obtained on the fibrous substrate. An additional important factor is the elastic compression restoring rate of said fibrous substrate.

For dispersion and fixation of aqueous monomer solution with uniform distribution, it is preferred to use a fibrous substrate having a unit weight of 15 to 50 g/m$^2$ and a compression restoring rate at least of 30%.

With the fibrous substrate at least partially containing hydrophobic fibers adapted to come into contact with water at an angle of 70 to 110°, the elastic compression restoring rate is improved, and the aqueous monomer solution and therefore the polymer particles are kept in spherical shape on the fibrous substrate with uniform distribution throughout the fibrous substrate.

When mixed with hot melt fibers and subjected to heat setting, the fibrous substrate is improved in its elastic compression restoring rate and also in strength as well as stability of its shape. For example, it is possible to use the fibrous substrate having a specific volume (bulk) less than 1.5 cc/g comprising web mixed with hot melt polyester fibers less than 45%, then loosely molded and finally subjected to heat setting.

Alternatively, such dispersion and fixation of the liquid-absorbent polymer particles on the fibrous substrate is achieved by uniformly mixing the fibers into the aqueous monomer solution and then polymerizing the mixture thereof, or grinding or splitting said polymerized mixture and then molding such mixture into a sheet followed by heat setting.

Preferably, a diffusion sheet 14 made of material such as tissue paper or ground pulp is integrally laminated on the upper and/or lower surfaces of the coolant carrier 10 prepared in the exemplary manners as have been described above by compressing said diffusion sheet 14 together with the fibrous substrate 12. With the coolant carrier 10 thus obtained, it has been found that liquid is uniformly absorbed into all the polymer particles and liquid holding ability, in other words, cooling ability is effectively improved.

The container 11 adapted to enclose the above mentioned coolant carrier 10 comprises liquid-permeable sheets 15, 16 defining upper and lower layers which are heet sealed along their outer peripheries 17 to seal the container 11.

Such container 11 has the opposite layers formed by the liquid-permeable sheets 15, 16 made of nonwoven fabric and thereby liquid-permeable layer sections 18 are provided all over these opposite layers. When the cooling pack utilizing such container 11 is immersed into coolant such as water, said coolant is rapidly introduced into the container and absorbed by the coolant carrier 10. The liquid-absorbent polymer particles 13 which is a component of the coolant carrier 10, have been fixed to the fibrous substrate 12, so no exudation of the polymer particles from the container 11 occurs before and after said liquid introduction and thus desired uniform liquid absorption is achieved. The cooling pack is then placed into a cooling apparatus such as refrigerator and is used for various cooling purpose after the liquid-absorbent polymer particles holding said liquid has been sufficiently refrigerated. The sheets 15, 16 defining said liquid-permeable layer sections 18 preferably have not only the liquid-permeability but also appropriate strength and, as material for such sheets, it is possible to use nonwoven fabric having a water pressure resistance of 200 to 300 mm H₂0 or less, or perforated plastic sheet or film having a high liquid permeability, or laminate thereof. Most preferably, however, nonwoven fabric is used. Such nonwoven fabric includes span lace, span bond, melt bond and nonwoven fabric of dry type.

By processing the nonwoven fabric with surfactant, a liquid-permeability under a low water pressure is significantly improved. However, nonwoven fabric of high liquid-permeability is high also in liquid holding ability and inconvenient in that, when a plurality of the cooling packs each utilizing the container made of such nonwoven fabric are stacked in a cooling apparatus, the containers of the respective cooling packs sometimes stick to one another as residual liquid held in nonwoven fabric is frozen, resulting in that the individual cooling packs cannot be separated from one another. With a consequence, said liquid residue must be removed from nonwoven fabric by drying the respective cooling packs prior to placement into the cooling apparatus.

Figure 3:
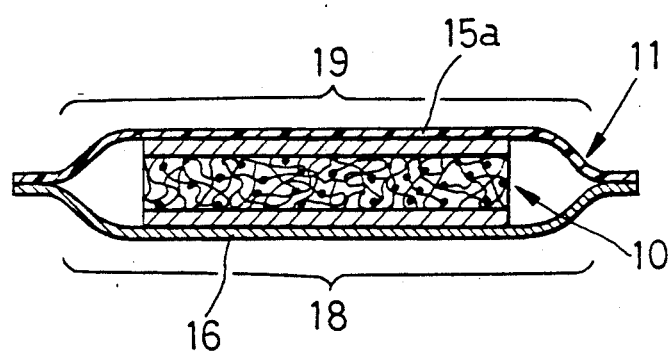
FIG. 3 is a view similar to FIG. 2, showning another embodiment of the present invention.

To eliminate such trouble, an embodiment of the cooling pack as shown by FIG. 3 is so constructed that the upper layer of the container 11 is formed by the liquid impermeable sheet 15a such as plastic sheet or film while the lower is formed by said liquid-permeable sheet 16, defining a liquid-impermeable layer section 19 and a liquid-permeable layer section 18, respectively. The remaining features are identical to the corresponding features of the previous embodiment shown by FIGS. 1 and 2.

When a plurality of the cooling packs each constructed as mentioned above are stacked so as to bring the liquid-permeable layer sections 18 in contact with the liquid-impermeable layer sections 19 in order to cool said packs efficiently at the same time, the containers 11 do not stick to one another even if the respective liquid-permeable layer sections 18 contain a certain amount of water residue and such residual water is frozen, since the liquid-impermeable layer section 19 being incontact with said liquid-permeable layer section 18 has a relatively high water repellency. Accordingly, even if said liquid-permeable layer section is formed from nonwoven fabric, the previously mentioned process of drying this nonwoven fabric is unnecessary.

Figure 4:
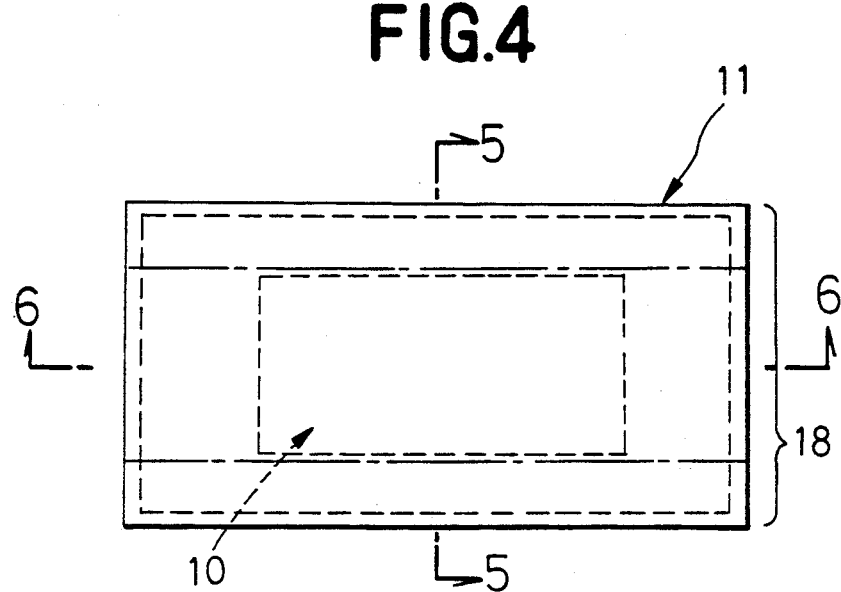
FIG. 4 is a plan view showing still another embodiment of the cooling pack according to the present invention.
Figure 5:
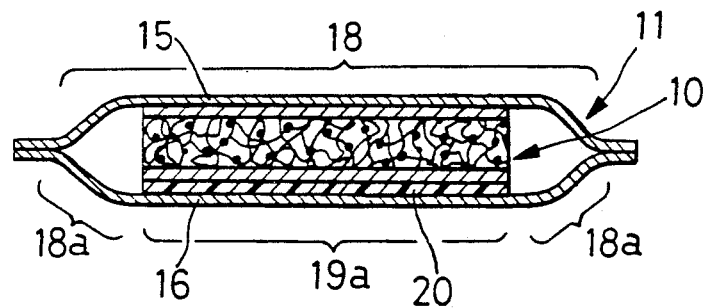
FIG. 5 is a sectional view taken along a line 5—5 in FIG. 4.
Figure 6:
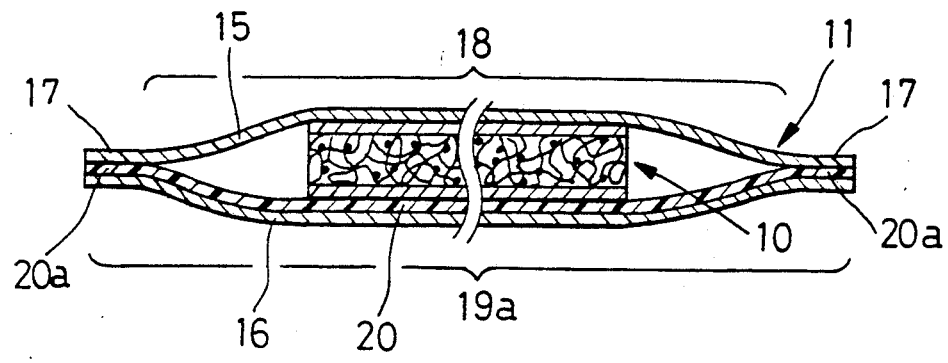
FIG. 6 is a sectional view taken along a line 6—6 in FIG. 4.

In an embodiment of the cooling pack as illustrated by FIGS. 4 through 6, for the same purpose as in the embodiment of FIG. 3, the upper and lower layers of the container 11 are formed by said liquid-permeable sheets 15, 16, respectively, and there is provided between the coolant carrier 10 enclosed by said container 11 and said lower liquid-permeable sheet 16 a liquid-impermeable sheet 20 such as plastic sheet or film which is substantially as wide as said coolant carrier 10 and extends longitudinally of said container 11 to longitudinally opposite ends 20a sandwiched by said both sheets 15, 16. By heat sealing the peripheral edges of the respective sheets 15, 16 together with said longitudinally opposite ends 20a of the liquid-impermeable sheet 20, the upper layer of the container defines the liquid-permeable layer section 18 and the lower layer of the container defines the combined liquid-permeable layer section 18a/liquid-impermeable layer section 19a. The remaining features are identical to the corresponding features of the embodiment as shown by FIGS. 1 and 2.

Figure 7:
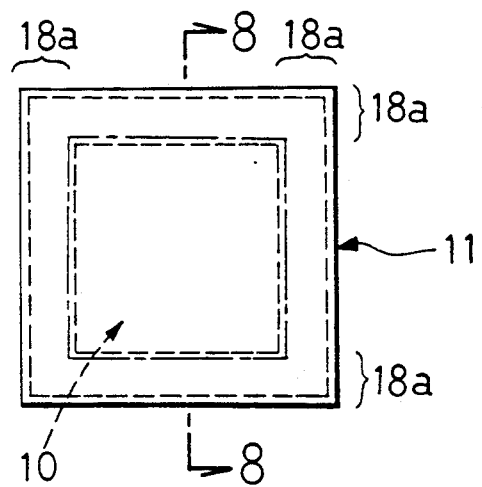
FIG. 7 is a plan view showing further another embodiment of the cooling pack according to the present invention.
Figure 8:
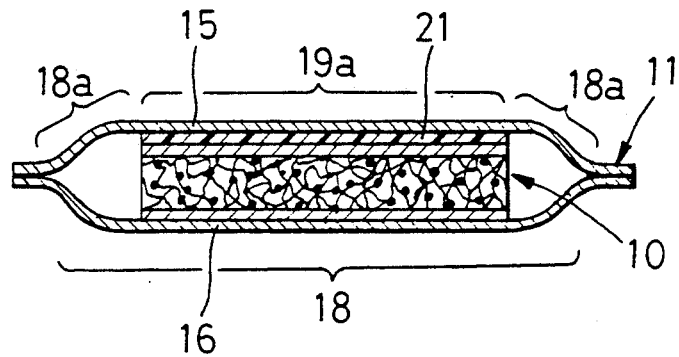
FIG. 8 is a sectional view taken along a line 8—8 in FIG. 7.

Also in an embodiment of the cooling pack as shown by FIG. 7 and 8, substantially for the same purpose as in the embodiment of FIG. 3, the upper and lower layers of the container are formed by said liquid-permeable sheets 15, 16, respectively, and at least the upper side of the coolant carrier 10 enclosed in said container is covered with a liquid-impermeable sheet 21 such as plastic sheet or film so that the upper layer of the container defines the combined liquid-permeable layer section 18a/liquid-impermeable layer section 19a while the lower layer of the container defines the liquid-permeable layer section 18.

Figure 9:
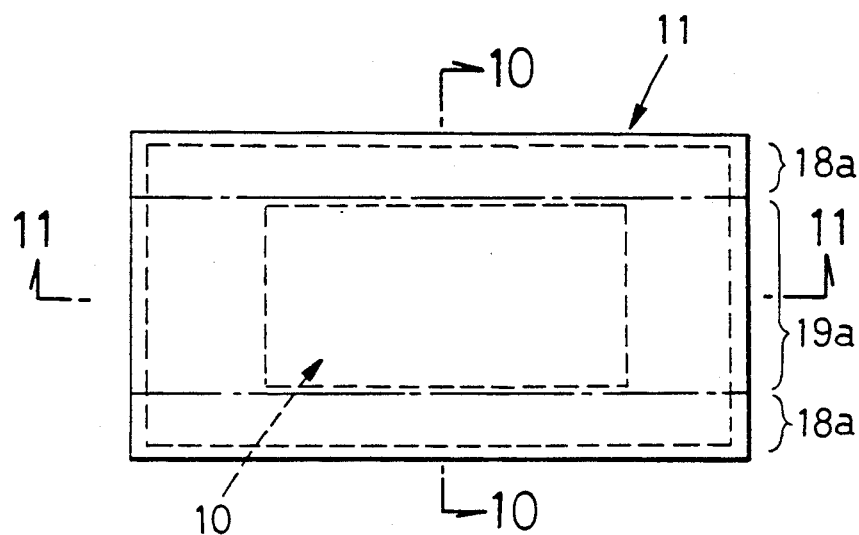
FIG. 9 is a plan view showing an additional embodiment of the cooling pack according to the present invention.
Figure 10:
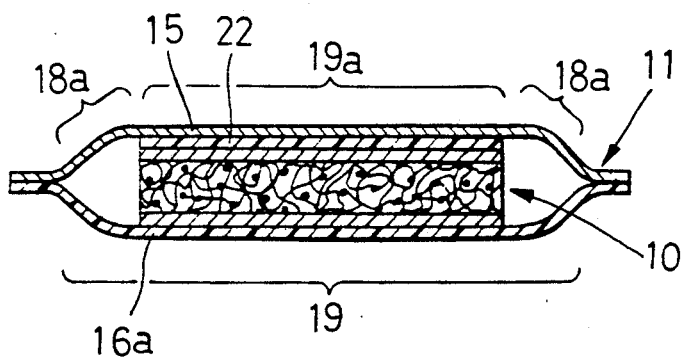
FIG. 10 is a sectional view taken along a line 10—10 in FIG. 9.
Figure 11:
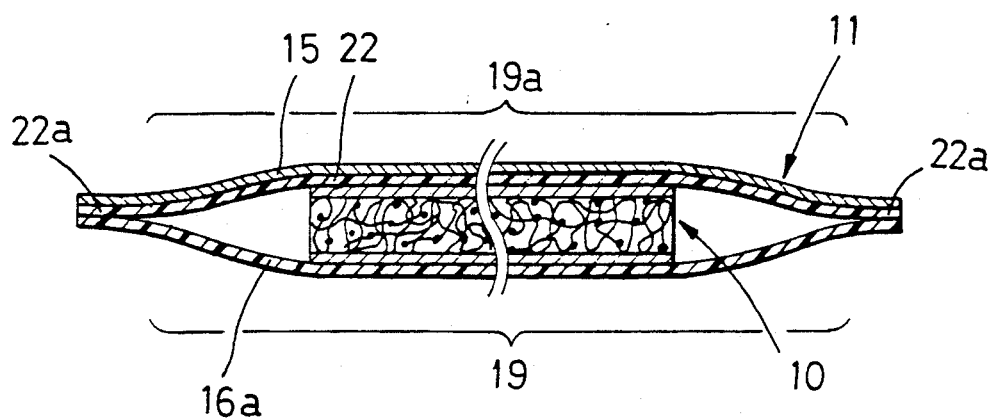
FIG. 11 is a sectional view taken along a line 11—11 in FIG. 9.

Also in an embodiment of the cooling pack as shown by FIGS. 9 through 11, for the same purpose as in the embodiment of FIG. 3, the upper and lower layers of the container 11 are formed by said liquid-permeable sheet 15 and a liquid-impermeable sheet 16a such as plastic sheet or film, respectively, and there is provided between the upper liquid-permeable sheet 15 and the coolant carrier 10 enclosed in said container a liquid-impermeable sheet 22 such as plastic sheet or film which is substantially as wide as said coolant carrier 10 and extends longitudinally of said container 11 to longitudinally opposite ends 22a sandwiched by said both sheets 15, 16a. By heat sealing the peripheral edges of the respective sheets 15, 16a together with said longitudinally opposite ends 22a of the liquid-impermeable sheet 22, the upper layer of the container defines the combined liquid-permeable layer section 18a/liquid-impermeable layer section 19a while the lower layer of the container defines the liquid-impermeable layer section 19. The remaining features are identical to the corresponding features of the embodiment shown by FIGS. 1 and 2.

Figure 12:
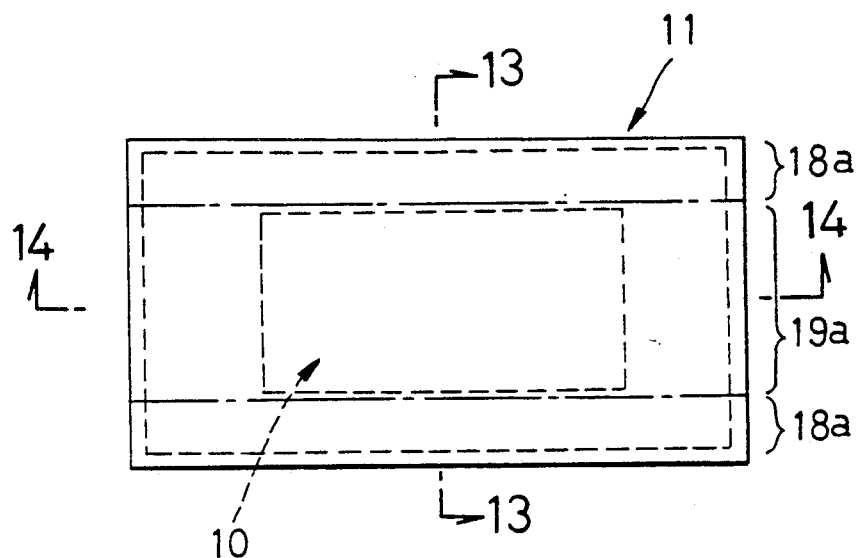
FIG. 12 is a plan view showing further additional embodiment of the cooling pack according to the present invention.
Figure 13:
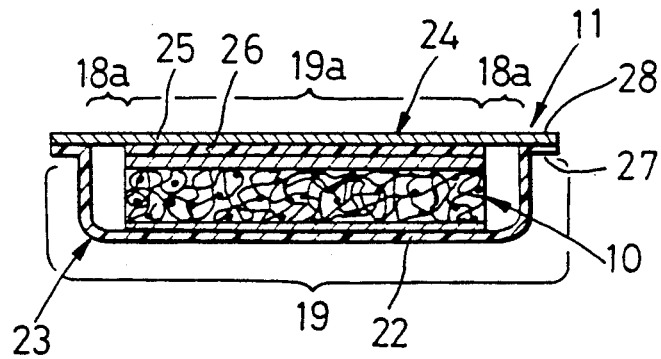
FIG. 13 is a sectional view taken along a line 13—13 in FIG. 12.
Figure 14:
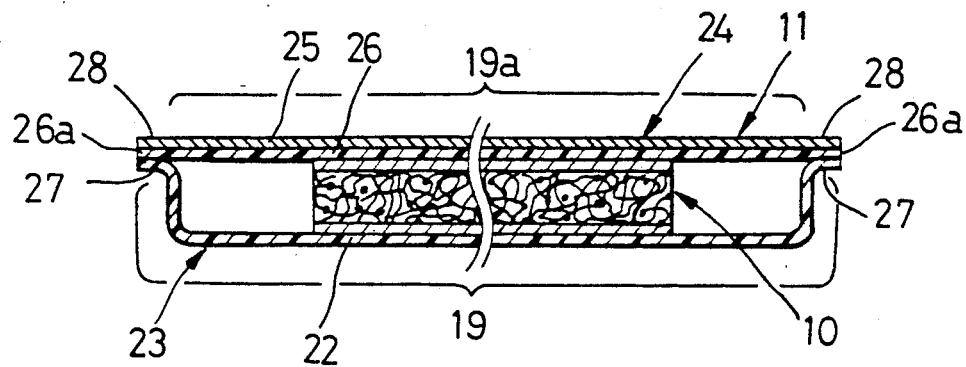
FIG. 14 is a sectional view taken along a line 14—14 in FIG. 12.

Similarly, in an embodiment of the cooling pack as illustrated by FIGS. 12 through 14, for the same purpose as in the embodiment of FIG. 3, the container 11 consists of an upwardly open box-shaped body 23 formed by plastic sheet and a cover 24 which comprises, in turn, fibrous nonwoven fabric 25 and a liquid-impermeable sheet 26 such as plastic sheet or film bonded to the inside surface of said nonwoven fabric 25 except said surfaces of transversely opposite sides each having an appropriate width. The box-shaped body 23 of the container 11 contains said coolant carrier 10 and supports the cover 24 on flanges 27 along longitudinally opposite ends of said box-shaped body 23. Thus, longitudinally opposite ends 26a of the liquid-impermeable sheet 26 is sandwiched between said flanges 27 and longitudinally opposite ends 28 of the cover 24. Said box-shaped body 23 and said cover 24 are hot sealed along their peripheral edges together with said longitudinally opposite ends 26a of the liquid-impermeable sheet 26 to seal the container 11. In this manner, the liquid-permeable layer section 18a are defined by the transversely opposite side margins of the cover 24 and the liquid-impermeable layer sections 19a, 19 are defined by the rest of the container 11. The remaining features are identical to the corresponding features of the embodiment shown by FIGS. 1 and 2.

As will be apparent from the cooling packs shown by FIGS. 6 through 14, the liquid-impermeable sheets 20, 21, 22, 26 may be located at least centrally on at least on the upper or lower layer of each cooling pack which is stacked on each other and therefore the desired object is achieved.

The expression used herein "liquid-impermeable layer section" dose not necessarily imply "perfect liquid-impermeability" in strict meaning, but covers various layer sections having features such as a relatively high water pressure resistance, a restricted free passage of liquid through those layer sections, or a minimized possibility of having liquid residue in those layer sections. For example, when nonwoven fabric layer section partially carries on its inner surface a plastic sheet or film as shown in the embodiments, such a layer section becomes substantially liquid-impermeable as said nonwoven fabric comes in tight-contact with said plastic sheet or film under a pressure of water introduced into the container. Particularly when said layer section is made of hydrophobic nonwoven fabric, the liquid residue held in said layer section carrying said plastic sheet or film is substantially less than that in the remaining layer section. As a result, if a plurality of the cooling packs are stacked with such layer sections being in contact with another cooling pack for refrigeration, the problem often encountered by prior art such that the individual cooling packs unseparably stick to one another is effectively avoided. If required, said plastic sheet or film may be bonded to said nonwoven fabric all over the surface or in an appropriate pattern.

As will be understood from the embodiments illustrated, the term herein used "container" implies a bag-shaped, box-shaped or similar container made of flexible or rigid material and having at least a pair of layers opposed to each other, which are substantially flat (or may be slightly curved so far as they can be deformed to flat condition) so that a plurality of the cooling packs can be vertically or horizontally stacked.

Preferably, volumes of the coolant carrier 10 and the container 11 are so dimensioned that the latter may effectively accommodate the former even after the former has absorbed an adequate quantity of liquid and its volume has correspondingly increased. Otherwise, the cooling pack might be sometimes disadvantageously deformed due to such increased volume of the former, though depending on the strength of the latter.

It should be understood that the liquid-impermeable sheets 20, 21, 22, 26 may be replaced by aluminium foil, if desired.

What is claimed is:

1. A cooling pack comprising at least one coolant carrier obtained by dispersing and fixing liquid absorbent polymer particles integrally on liquid absorbent fibrous substrate with substantially uniform distribution and successively forming said substrate into a sheet or a mat, and a flat bag-shape container having at least first and second flat layers opposed to each other to enclose said coolant carrier, wherein said first flat layer of said container is made of liquid-permeable fibrous nonwoven fabric, said nonwoven fabric carrying on the inside thereof at least along the central area except the transversely opposite side areas a liquid-impermeable plastic sheet or film so as to cover at least a major portion of said coolant carrier to which said liquid-impermeable plastic sheet or film is opposed; and wherein said second flat layer is made of a liquid-impermeable plastic sheet or film.

2. A cooling pack comprising at least one coolant carrier obtained by dispersing and fixing liquid absorbent polymer particles integrally on liquid absorbent fibrous substrate with substantially uniform distribution and successively forming said substrate into a sheet or a mat, and a box-shape container having at least first and second flat layers opposed to each other to enclose said coolant carrier, wherein said first flat layer of the container is formed by liquid-permeable fibrous nonwoven fabric, said nonwoven fabric carrying on the inside thereof at least along the central area except the transversely opposed side areas a liquid-impermeable plastic sheet or film so as to cover at least a major portion of said coolant carrier to which said liquid-impermeable plastic sheet or film is opposed, and wherein said second flat layer and the remaining layer section are formed by liquid-impermeable plastic sheet or film.

3. A cooling pack that includes in combination
   (1) a coolant carrier that is in the form of a mat that is composed of
      (a) a mass of liquid absorbent fibrous material, and
      (b) a plurality of separated liquid absorbent spherical polymer particles dispersed in said fibrous material and fixed integrally to said fibrous material by partially enclosing component fibers, said polymer particles being able to absorb a quantity of water between several ten times and several hundred times their own weight, and
   (2) a container enclosing said coolant carrier, said container comprising a pair of opposed substantially flat sheets, at least one of said sheets permitting water access to said coolant carrier.

4. A cooling pack that includes in combination
   (1) a coolant carrier that is in the form of a mat that is composed of
      (a) a mass of liquid absorbent fibrous material, and
      (b) a plurality of separated liquid absorbent spherical polymer particles dispersed in said fibrous material and fixed integrally to said fibrous material by partially enclosing component fibers, said polymer particles being able to absorb a quantity of water between several ten times and several hundred times their own weight, and
   (2) a container enclosing said coolant carrier, said container comprising a pair of opposed substantially flat sheets, at least one of said sheets permitting water access to said coolant carrier, at least one of said sheets being formed, at least centrally, with a liquid impermeable section covering at least a major portion of one side of the coolant carrier that is closest to said sheet.

* * * * *